(12) United States Patent
Narula et al.

(10) Patent No.: US 7,074,967 B1
(45) Date of Patent: Jul. 11, 2006

(54) DERIVATIVES OF 3-CYCLOPROPYL-1-PROPANONE COMPOUNDS AND THEIR USE IN PERFUME COMPOSITIONS

(75) Inventors: Anubhav P. S. Narula, Hazlet, NJ (US); Edward Mark Arruda, Cliffwood, NJ (US); Franc T. Schiet, Naarden (NL)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/286,180

(22) Filed: Nov. 23, 2005

(51) Int. Cl.
*C07C 49/21* (2006.01)
*A61K 7/46* (2006.01)

(52) U.S. Cl. .................. 568/376; 568/377; 512/22; 512/27

(58) Field of Classification Search ............... None
See application file for complete search history.

(56) References Cited

U.S. PATENT DOCUMENTS 4,534,891 A * 8/1985 Boden et al. ............ 510/101

* cited by examiner

*Primary Examiner*—Sikarl A. Witherspoon
(74) *Attorney, Agent, or Firm*—Alexander Migirov

(57) ABSTRACT

The present invention is directed to novel 3-cyclopropyl-1-propanone compounds of the general formula

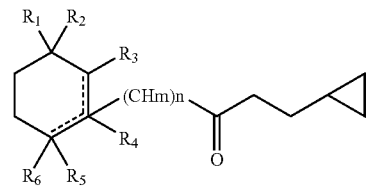

wherein $R_1$, $R_2$, $R_3$, $R_4$, $R_5$ and $R_6$ each independently is a hydrogen or a straight, branched or cyclic hydrocarbon moiety consisting of less then 10, preferably less then 5 carbon atoms and containing single and/or double bonds; wherein m and n each independently is an integer of 0–10; and wherein the dotted line represents a possible double bond.

10 Claims, No Drawings

DERIVATIVES OF 3-CYCLOPROPYL-1-PROPANONE COMPOUNDS AND THEIR USE IN PERFUME COMPOSITIONS

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allows perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel 3-cyclopropyl-1 propanone compounds, represented by the general structure of Formula I set forth below:

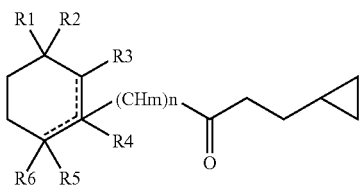

Formula I wherein R1, R2, R3, R4, R5 and R6 are each independently a hydrogen or a straight, branched or cyclic hydrocarbon moiety consisting of less then 10, preferably less then 5 carbon atoms and containing single and/or double bonds;

wherein m and n each independently is an integer of 0–10; and wherein the dotted line represents a possible double bond.

Another embodiment of the invention is a method for enhancing a perfume composition by incorporating an olfactory acceptable amount of the compounds provided above.

These and other embodiments of the present invention will be apparent by reading the following specification.

DETAILED DESCRIPTION OF THE INVENTION

In Formula I above, R1, R2, R3, R4, R5 and R6 each independently represent a straight, branched or cyclic hydrocarbon moiety consisting of less then 10, preferably less then 5 carbon atoms and containing single and/or double bonds.

Suitable straight hydrocarbon moieties include ethyl, propyl, butyl, pentyl, hexyl, and the like. Suitable branched hydrocarbon moieties include isopropyl, sec-butyl, tert-butyl, 2-ethyl-propyl, and the like. Suitable hydrocarbon moieties containing double bonds include ethene, propene, 1-butene, 2-butene, penta-1-3-deine, hepta-1,3,5-triene and the like. Cyclic hydrocarbons include cyclopropyl, cyclobutyl, cyclohexyl, phenyl and the like.

In the preferred embodiment of the invention, the novel compounds of the present invention are represented by the following structures:

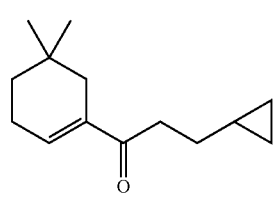

Formula II

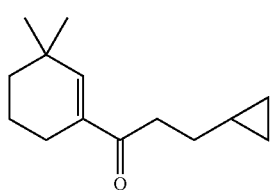

Formula III

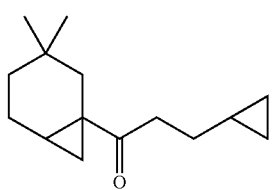

Formula IV

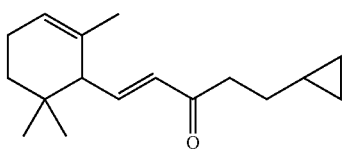

Formula V

Those with the skill in the art will appreciate that the compound of Formula II is 3-cyclopropyl-1-(5,5-dimethyl-cyclohex-1-enyl)-1-propanone, the compound of Formula III is 3-cyclopropyl-1-(3,3-dimethyl-cyclohex-1-enyl)-1-propanone; the compound of Formula IV is 3-cyclopropyl-1-(3,3-dimethyl-bicyclo[4.1.0]hept-1-yl)-1-propanone and the compound of Formula V is 5-cyclopropyl-1-(2,6,6-trimethyl-cyclohex-2-enyl)-1-pentenone.

The table below lists additional compounds derived from Formula I that are described in the present invention:

| Structure | Name |
|---|---|
| 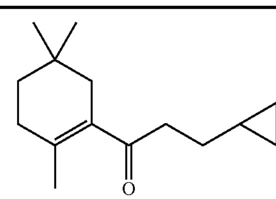 | 3-cyclopropyl-1-(2,5,5-trimethyl-cyclohex-1-enyl)-1-propanone |

| Structure | Name |
|---|---|
| 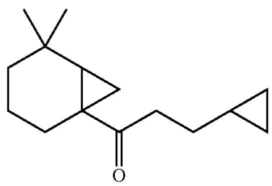 | 3-cyclopropyl-1-(5,5-dimethyl-bicyclo[4.1.0]hept-1-yl)-1-propanone |
| 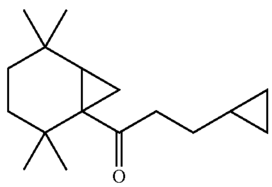 | 3-cyclopropyl-1-(2,2,5,5-tetramethyl-bicyclo[4.1.0]hept-1-yl)-1-propanone |
| 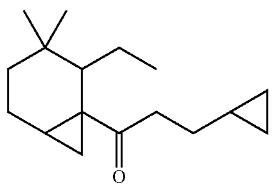 | 3-cyclopropyl-1-(2-enyl-3,3-dimethyl-bicyclo[4.1.0]hept-1-yl)-1-propanone |
| 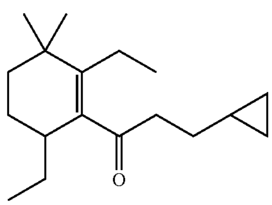 | 3-cyclopropyl-1-(2,6-diethyl-3,3-dimethyl-cyclohex-1-enyl)-1-propanone |
| 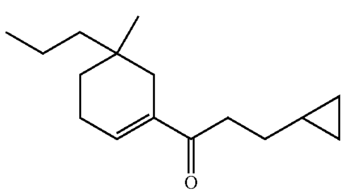 | 3-cyclopropyl-1-(5-methyl-5-propyl-cyclohex-1-enyl)-1-propanone |
| 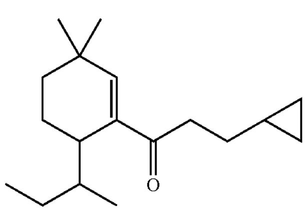 | 1-(6-sec-butyl-3,3-dimethyl-cyclohex-1-enyl)-3-cyclopropyl-1-propanone |
| 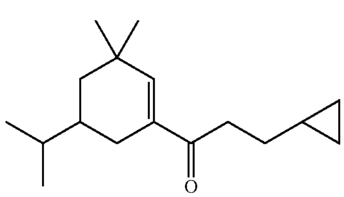 | 3-cyclopropyl-1-(5-isopropyl-3,3-dimethyl-cyclohex-1-enyl)-1-propanone |
| | 1-(4-sec-butyl-5,5-dimethyl-cyclohex-1-enyl)-3-cyclopropyl-1-propanone |
| | 1-cyclopropyl-7-(6-ethyl-2,5,5,-trimethyl-cyclohex-1-enyl)-4-hepten-3-one |

The compounds of the present invention may be prepared from the corresponding compounds containing a double bond by following a Simmon-Smith cyclopropanation reaction such as described below:

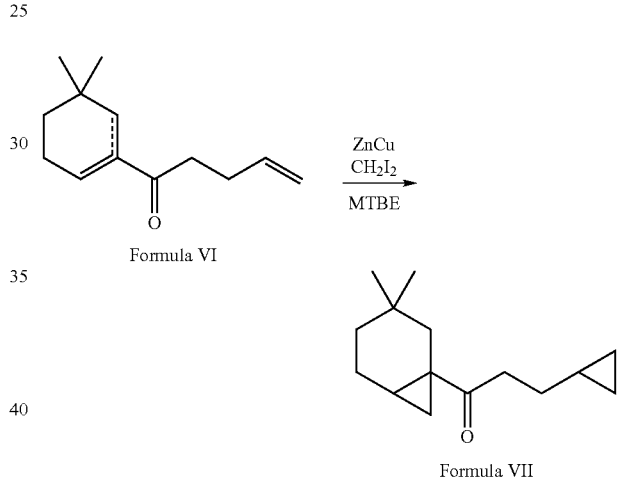

Formula VI

Formula VII

The alkene of Formula VI used in the above reaction to prepare the compounds of the present invention is a commercially available material that may be obtained from Aldrich.

Those with skill in the art will recognize that some of the compounds of the present invention have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as High Performance Liquid Chromatography ("HPLC") and particularly gel chromatography and solid phase microextraction ("SPME").

We have discovered that the compounds of Formulae II–V have a very strong herbal, galbanum, green, pineapple odor and are well suited for use as a fragrance ingredient.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. IFF as used in the examples is understood to mean International Flavors & Fragrances Inc., New York, N.Y., USA.

EXAMPLE A

Preparation of 3-cyclopropyl-1-(5,5-dimethyl-cyclohex-1-enyl)-1-propanone

To a dry 500 ml multi-neck round bottom flask fitted with an air stirrer, nitrogen inlet condenser and an addition funnel 8 g of Zn—Cu, 70 ml of Methyl Tertiary Butyl Ether (MTBE) and 3 crystals of $I_2$ were added and stirred. 23 g of $CH_2I_2$ was added while stirring. A heating source was applied to the mixture. 22 g of 4-penten-1one, 1-(5,5-dimethyl-1-cyclohexen-1-yl) was added dropwise over 20 minutes. The mixture was aged for 7.5 hours. The mixture was quenched with saturated $NH_4Cl$, aqueous layer separated and the organic layer washed with 200 ml of water. The organic layer was then dried over anhydrous $MgSO_4$.

The NMR of the 3-cyclopropyl-1-(5,5-dimethyl-cyclohex-1-enyl)-1-propanone is as follows: 0.6 ppm (m, 4H); 0.7 ppm (m, 1H); 0.8 ppm (s, 3H); 0.9 ppm (s, 4H); 1.0 ppm (s, 2H); 1.1 ppm (s, 7H); 1.2 ppm (m, 2H); 1.2 ppm (m, 1H); 1.3 ppm (m, 1H); 2.1 ppm (d, 1H); 2.2 ppm (m, 1H); 3.3 ppm (s, 3H).

EXAMPLE B

Preparation of 3-cyclopropyl-1-(3,3-dimethyl-cyclohex-1-enyl)-1-propanone

To a dry 200 ml multi-neck round bottom flask fitted with an air stirrer, nitrogen inlet condenser and an addition funnel 1 g of Zn—Cu, 30 ml of Methyl Tertiary Butyl Ether (MTBE) and 1 crystal of $I_2$ were added and stirred. 3,3 g of $CH_2I_2$ was via syringe. The mixture was heated maintained at 60° C. 1.97 g of 4-penten-1one, 1-(3,3-dimethyl-1-cyclohexen-1-yl) was added in one portion. The mixture was aged for 7.5 hours. The mixture was quenched with saturated $NH_4Cl$, aqueous layer separated and the organic layer washed with 200 ml of water. The organic layer was then dried over anhydrous $MgSO_4$. The NMR of the 3-cyclopropyl-1-(3,3-dimethyl-cyclohex-1-enyl)-1-propanone is as follows: 0.2 ppm (s, 1H); 0.8 ppm (m, 10H); 1.0 ppm (d, 8H); 1.2 ppm (m, 3H); 1.3 ppm (m, 1H); 1.5 ppm (m, 2H); 1.6 ppm (s, 2H); 1.6–1.7 ppm (m, 1H); 1.8 ppm (d, 1H); 2.3 ppm (d, 1H); 3.3 ppm (m, 1H); 3.7 ppm (m, 1H).

EXAMPLE C

Preparation of 3-cyclopropyl-1-(3,3-dimethyl-bicyclo[4.1.0]hept-1-yl)-1-propanone To a dry 200 ml multi-neck round bottom flask fitted with an air stirrer, nitrogen inlet condenser and an addition funnel 8 g of Zn—Cu, 75 ml of Methyl Tertiary Butyl Ether (MTBE) and a few crystals of $I_2$ were added and stirred. 52 g of $CH_2I_2$ was added and the mixture was heated to 60° C. 19 g of 4-penten-1one, 1-(5,5-dimethyl-1-cyclohexen-1-yl) was added over a period of 30 minutes. The mixture was aged for 10 hours. The mixture was quenched with saturated $NH_4Cl$, aqueous layer separated and the organic layer washed with two portions of 100 ml of brine. The organic layer was then dried over anhydrous $MgSO_4$.

The NMR of the 3-cyclopropyl-1-(3,3-dimethyl-bicyclo[4.1.0]hept-1-yl)-1-propanone is as follows: 0.0 ppm (s, 2H); 0.4 ppm (s, 2H); 0.6 ppm (s, 1H); 0.7 ppm (s, 1H); 0.8 ppm (d, 6H); 1.0 ppm (m, 1H); 1.1 ppm (m, 2H); 1.4 ppm (m, 3H); 1.6 ppm (m, 1H); 1.8 ppm (d, 1H); 1.9 ppm (m, 1H); 2.4 ppm (m, 2H); 2.6 ppm (d, 1H).

EXAMPLE D

Preparation of 5-cyclopropyl-1-(2,6,6-trimethyl-cyclohex-2-enyl)-1-pentenone

To a dry 200 ml multi-neck round bottom flask fitted with an air stirrer, nitrogen inlet condenser and an addition funnel 8 g of Zn—Cu and 100 ml of Methyl Tertiary Butyl Ether (MTBE) were added and stirred. 23 g of $CH_2I_2$ was added via syringe. The mixture was heated maintained at 40° C. 12 g of 1-(2,6,6-trimethyl-cyclohex-2-enyl)-hepta-1,6-dien-3-one was added drop-wise. The mixture was aged for 7.5 hours. The mixture was quenched with saturated $NH_4Cl$, aqueous layer separated and the organic layer washed with 200 ml of water. The organic layer was then dried over anhydrous $MgSO_4$. The NMR of the 5-cyclopropyl-1-(2,6,6-trimethyl-cyclohex-2-enyl)-1-pentenone is as follows: 0.1 ppm (m, 2H); 0.4 ppm (m, 2H); 0.7 ppm (m, 1H); 0.8 ppm (m, 4H); 0.9 ppm (m, 4H); 1.0 ppm (m, 2H); 1.2 ppm (m, 2H); 1.4 ppm (m, 1H); 1.5 ppm (m, 2H); 1.6 ppm (m, 3H); 2.1 ppm (s, 2H); 2.3 ppm (d, 1H); 2.4 ppm (m, 1H); 2.7 ppm (m, 2H); 5.5 ppm (1, 1H); 6.1 ppm (d, 1H); 6.7 ppm (m, 1H).

EXAMPLE E

DEMONSTRATION FORMULA (SHOWER GEL) WITH 3-cyclopropyl-1-(3,3-dimethyl-bicyclo[4.1.0]hept-1-yl)-1-propanone

| | |
|---|---|
| Aldehyde AA Triplal | 2 |
| Allyl Amyl Glycolate | 20 |
| Ambroxan | 1 |
| Benzyl Acetate | 6 |
| 3-cyclopropyl-1-(3,3-dimethyl-bicyclo[4.1.0]hept-1-yl)-1-propanone | 6 |
| Damascone Delta | 10 |
| Dihydro Myrcenol | 300 |
| Geranium Oil | 2 |
| Hedione | 70 |
| Koavone | 60 |
| Lavandin Oil | 5 |
| Linalool | 140 |
| Linalyl Acetate | 175 |
| Lyral | 60 |
| Menthol | 20 |
| Methyl Beta Naphtyl Ketone | 5 |
| Methyl Anthranilate | 18 |
| Methyl Octin Carbonate 1% in Dipropyleneglycol | 12 |
| Phenyl Ethyl Alcohol | 15 |
| Pine Oil | 30 |
| Precyclemone B | 20 |
| Styralyl Acetate | 5 |
| Terpinyl Acetate | 15 |
| Veramoss | 3 |
| Total weight | 1000.00 |

This fragrance was described as having herbal, galbanum, green and pineapple odor notes.

EXAMPLE F

Demonstration formula (shampoo) with 3-cyclopropyl-1-(5,5-dimethyl-cyclohex-1-enyl)-1-propanone

| | |
|---|---|
| 3-Hydroxy-2-Methyl-4-Pyrone 10% in Dipropyleneglycol | 5.00 |
| Aldehyde AA Triplal | 5.00 |
| Bergamal | 5.00 |
| Blackcurrant Bud Absolute MD LMR 10% in Dipropyleneglycol | 10.00 |
| Cassifix | 513.00 |
| Cis-2-Methyl-4-Propyl-1,3-Oxathiane 10% in Dipropyleneglycol | 6.00 |
| Damascenone | 5.00 |
| 3-cyclopropyl-1-(5,5-dimethyl-cyclohex-1-enyl)-1-propanone | 60.00 |
| Ethyl Butyrate | 2.50 |
| Ethyl Caproate | 2.50 |
| Hedione | 150.00 |
| Iso Amyl Butyrate | 3.00 |
| Mangone 1% in Dipropyleneglycol | 5.00 |
| Menthyl Acetate | 20.00 |
| Methoxy Phenyl Butanone | 50.00 |
| Phenoxanol | 50.00 |
| Pinene, Alpha | 5.00 |
| Pinene, Beta | 25.00 |
| Styralyl Acetate | 10.00 |
| Total weight | 1000.00 |

This fragrance was described as having herbal, galbanum, green and pineapple odor notes.

What is claimed is:

1. A compound of formula

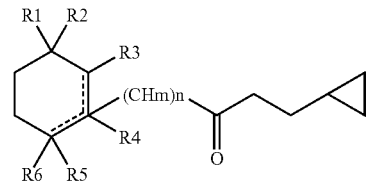

wherein R1, R2, R3, R4, R5 and R6 each independently is a hydrogen or a straight, branched or cyclic hydrocarbon moiety consisting of less then 10 carbon atoms and containing single and/or double bonds; wherein m and n each independently is an integer of 0–10; and wherein the dotted line represents a possible double bond.

2. A compound of claim 1, wherein R1, R2, R3, R4, R5 and R6 each independently is a straight, branched or cyclic hydrocarbon moiety consisting of less then 5 carbon atoms.

3. A method of improving, enhancing or modifying a fragrance formulation through the addition of an olfactory acceptable amount of the compound of claim 1.

4. The method of claim 3 wherein the fragrance is incorporated into a product selected from perfumes, colognes, toilet waters, cosmetic products, personal care products, fabric care products, cleaning products and air fresheners.

5. The method of claim 4 wherein the cleaning product is selected from the group consisting of detergents, dishwashing compositions, scrubbing compounds and window cleaners.

6. The method of claim 3 wherein the amount incorporated into a fragrance is from about 0.005 to about 10 weight percent.

7. The method of claim 3, wherein the amount incorporated into a fragrance is from about 0.5 to about 8 weight percent.

8. The method of claim 3, wherein the amount of incorporated into a fragrance is from about 1 to about 7 weight percent.

9. A fragrance formulation containing an olfactory effective amount of the compound of claim 1.

10. A fragrance product containing a compound of claim 1.

* * * * *